(12) United States Patent
Loch et al.

(10) Patent No.: US 6,820,057 B1
(45) Date of Patent: Nov. 16, 2004

(54) TELEMEDICINE SYSTEM

(75) Inventors: Andrew Loch, Nerang (AU); Kim Norman Barnett, Tamborine (AU); Bruce Richard Satchwell, Runaway Bay (AU); James Edward Fitzgerald, Manly (AU)

(73) Assignee: Ventracor Limited, Chatswood (AU)

( * ) Notice: Subject to any disclaimer, the term of this patent is extended or adjusted under 35 U.S.C. 154(b) by 0 days.

(21) Appl. No.: 09/319,392

(22) Filed: May 28, 1999

(30) Foreign Application Priority Data

Nov. 29, 1996 (AU) .............................................. PO 3943
Jan. 10, 1997 (AU) .............................................. PO 4553

(51) Int. Cl.$^7$ ................................................. A61F 2/00
(52) U.S. Cl. ................................ 705/2; 705/3; 600/300
(58) Field of Search .............................. 705/1, 2, 3, 4; 600/300, 512, 513; 128/903, 904; 707/104.1

(56) References Cited

U.S. PATENT DOCUMENTS

| | | | |
|---|---|---|---|
| 5,434,611 A | | 7/1995 | Tamura |
| 5,944,659 A | * | 8/1999 | Flach et al. ................. 600/300 |
| 6,282,441 B1 | * | 8/2001 | Raymond et al. ........... 600/513 |

FOREIGN PATENT DOCUMENTS

| | | |
|---|---|---|
| CA | 2125300 A | 11/1995 |
| EP | 734140 A2 | 9/1996 |
| WO | WO 95/16970 A | 6/1995 |

OTHER PUBLICATIONS

Proceedings of the SPIE—The International Society for Optical Engineering, vol. 2711, pp. 354–362, Jul. 1996, P. deBlas et al "Telemedicina: A Multimedia Broadband Teleradiology and Radiosurgery Project".
Proceedings of the SPIE—The International Society for Optical Engineering, vol. 2417, pp. 116–129, May 1995, L. Rodney Long et al "An application–level technique for faster transmission of large images on the internet".
Telematics and Informatics, vol. 11, No. 2, pp. 127–135, 1994, Donald F. Parson "The Impact of Information Technology on Health Care: A practitioner's prespective".
IEEE Communications Magazine, vol. 31, No. 1, Jan. 1993, S. Akselsen et al "Telemedicine and ISDN" pp. 46–51.
Proceedings, Computers in Cardiology, pp. 595–598, 1991, M.T. Arredondo et al "A Telemedicine approach for hypertension care".

* cited by examiner

Primary Examiner—Sam Rimell
(74) Attorney, Agent, or Firm—J. Mark Holland & Assoc.

(57) ABSTRACT

A method and system for communication of patient data acquired from a patient (13) involving the use of a predetermined communications protocol (48, 49, 50) whereby patient data is communicable from a patient location to an analysis location. In a preferred form, the patient data has appended to its supplementary data which can include address information and identity information.

26 Claims, 10 Drawing Sheets

Block Type 2 (Biolog/Paceview Single Lead)

| Parameter | Data Type | Example |
|---|---|---|
| Data length | unsigned int. | 17 (25 for Simultaneous 12 Lead) |
| Block Type | unsigned char. | 2 |
| Sampling Interval (us) | unsigned int. | 3333 |
| Device Serial Number | unsigned int. | 1234 |
| Device Hardware Version | unsigned char. | eg. 22 for V2A |
| Device Software Version | unsigned char. | eg. 24 for V2.4 |
| Device Type | 3 bits | 0=Biolog, 1=Paceview |
| Filter Frequency | 1 bit | 0=50Hz, 1=60Hz |
| Pacing Detection | 1 bit | 0=Disabled, 1=Enabled |
| Pacing Detected | 1 bit | 0=None Detected, 1=Detected |
| Reserved | 2 bits | |
| Event Date - Day | unsigned char. | BCD |
| Event Date - Month | unsigned char. | BCD |
| Event Date - Year | unsigned char. | BCD |
| Event Time - Hour | unsigned char. | BCD |
| Event Time - Minute | unsigned char. | BCD |
| Lead ID (Rhythm strip/SL) | unsigned char. | 1...12=1...V6, 0=Single Lead |
| Gain Scale | unsigned char. | units per mV |
| TT Scaling | unsigned char. | Hz per mV |
| Length of record (samples) | unsigned int. | Max.=65535 |

Extension for 6 digit Serial Numbers:

| Device Serial Number (high byte) | unsigned char. | |
|---|---|---|

Extension for Simultaneous 12 Lead Cable data:

| Device Serial Number (Cable) | unsigned 24 bit | 123456 |
|---|---|---|
| Device Hardware Version (Cable) | unsigned char. | eg. 11 for V1A |
| Device Software Version (Cable) | unsigned char. | eg. 10 for V1.0 |
| Resolution (nV) | unsigned int. | nV per unit |

*Fig. 9*

TELEMEDICINE SYSTEM

INTRODUCTION

The present invention relates to a telemedicine system and, more particularly, but not exclusively, to a system and component parts thereof adapted to acquire, record, transmit and analyse or have analysed ECG data and like patient data.

BACKGROUND

The word "telemedicine" is derived from words which imply the meaning far or distant medicine. The thrust and aim of "telemedicine" is to utilise electronic communication systems to transmit medical data in ways which allow the bringing to bear of cost effective high level expertise to interpretation of the information whilst also rendering the acquisition of the information as convenient as possible for the patient.

It is at least one object of the present invention to provide a system which allows the achievement of a practicable telemedicine system.

It is a further particular object of the invention to provide a system which can transmit time varying patient data in real time or near real time from one location to another.

It is another further particular object of at least a preferred embodiment of the invention to allow the transmission of such data over the interconnectable network of computers commonly called the "internet".

Electrocardiograph (ECG) recording has now been practiced for some decades. What is recorded is the electrical activity of the heart obtained by the attachment of conducting electrodes and through which the waveforms characteristic of heart activity can be obtained for analysis.

Whilst the basic principles have been known for some time the emphasis now is on obtaining wave forms which reflect a patient's heart operation over a period of days or weeks and at a variety of heart rates and stress levels. Obtaining this wealth of data requires sophisticated methods and apparatus to capture the information and then to ensure the information obtained is properly capitalised upon.

It is an object of the present invention to provide a telemedicine system and component parts therefore which allows the obtaining, storage and analysis of ECG data and like patient data which is on the one hand as convenient as possible for the patient and on the other hand capitalises on the volume of data obtained.

BRIEF DESCRIPTION OF INVENTION

Accordingly, in one broad form of the invention, there is provided a method of communication of patient data acquired from a patient; said method including arranging a predetermined communications protocol whereby patient data is communicable from a patient location to an analysis location.

Preferably said method is implemented by a system which includes at least the following components:

(a) patient data acquisition apparatus
(b) patient data transmission apparatus
(c) patient data reception apparatus
(d) patient data storage and analysis apparatus.

In a particular preferred form said storage and analysis apparatus is implemented on a personal computer.

In a further particular preferred form said patient data transmission apparatus additionally includes supplementary data insertion means.

Preferably said patient data is encoded for transmission in a first format whilst said supplementary data is encoded for transmission in a second format.

Preferably a unique identifier is given to each said patient data storage and analysis apparatus.

Preferably said unique identifier is embedded in a software portion comprising part of said patient data storage and analysis apparatus.

Preferably said patient data storage and analysis apparatus includes a personal computer arranged to execute a patient data storage and analysis program.

Preferably said patient data storage and analysis program includes customisable/user manipulable data base elements.

Preferably said patient data is encoded for transmission in a first format whilst said supplementary data is encoded for transmission in a second format.

Preferably said supplementary data comprises patient data and/or patient data acquisition apparatus identification data.

In a particular preferred form said patient data is ECG data.

In a further broad form of the invention there is provided a system for communication of patient data from a patient location to a remote storage and analysis location; said system including means for transmitting said patient data on a predetermined signal encoded according to a predetermined protocol whereby said patient data is communicable from said patient location to said analysis location.

Preferably said predetermined signal comprises a modulated audio tone.

Preferably said modulated audio tone is a frequency modulated (FM) audio tone.

Preferably said modulated audio tone has a centre frequency between 1,000 and 3,000 Hertz.

Preferably said centre frequency is approximately 1,900 Hertz.

Preferably said tone is frequency modulated at a rate of 100 Hertz per millivolt.

Preferably said predetermined protocol comprises direct modulation of an analogue wave form representing said patient data which is preceded by and recognised by a zero signal of predetermined duration.

Preferably said predetermined signal includes said patient data and supplementary data; said supplementary data comprising data pertaining to the circumstances of measurement of said clinical data.

Preferably said supplementary data is digitally encoded in a wave form suitable for frequency modulation of a carrier tone in the audio range.

Preferably said predetermined protocol includes a series of synchronization pulses which immediately precede and signal the presence of a signal containing said supplementary data.

In a particular preferred form said patient data is transmitted as digitised packets.

In a further particular preferred form said system includes a server computer adapted to receive said digitised packets of patient data.

Preferably said server computer is adapted to transmit program data and patient data in the form of digitised packets to a remote computer whereby said remote computer can execute said program data in order to display and/or interpret said patient data.

BRIEF DESCRIPTION OF DRAWINGS

Embodiments of the invention will now be described with reference to the accompanying drawings wherein:

FIG. 9 illustrates the data block structure where the data acquisition device is a biolog ECG single lead device.

DETAILED DESCRIPTION OF PREFERRED EMBODIMENTS

Figure 1:
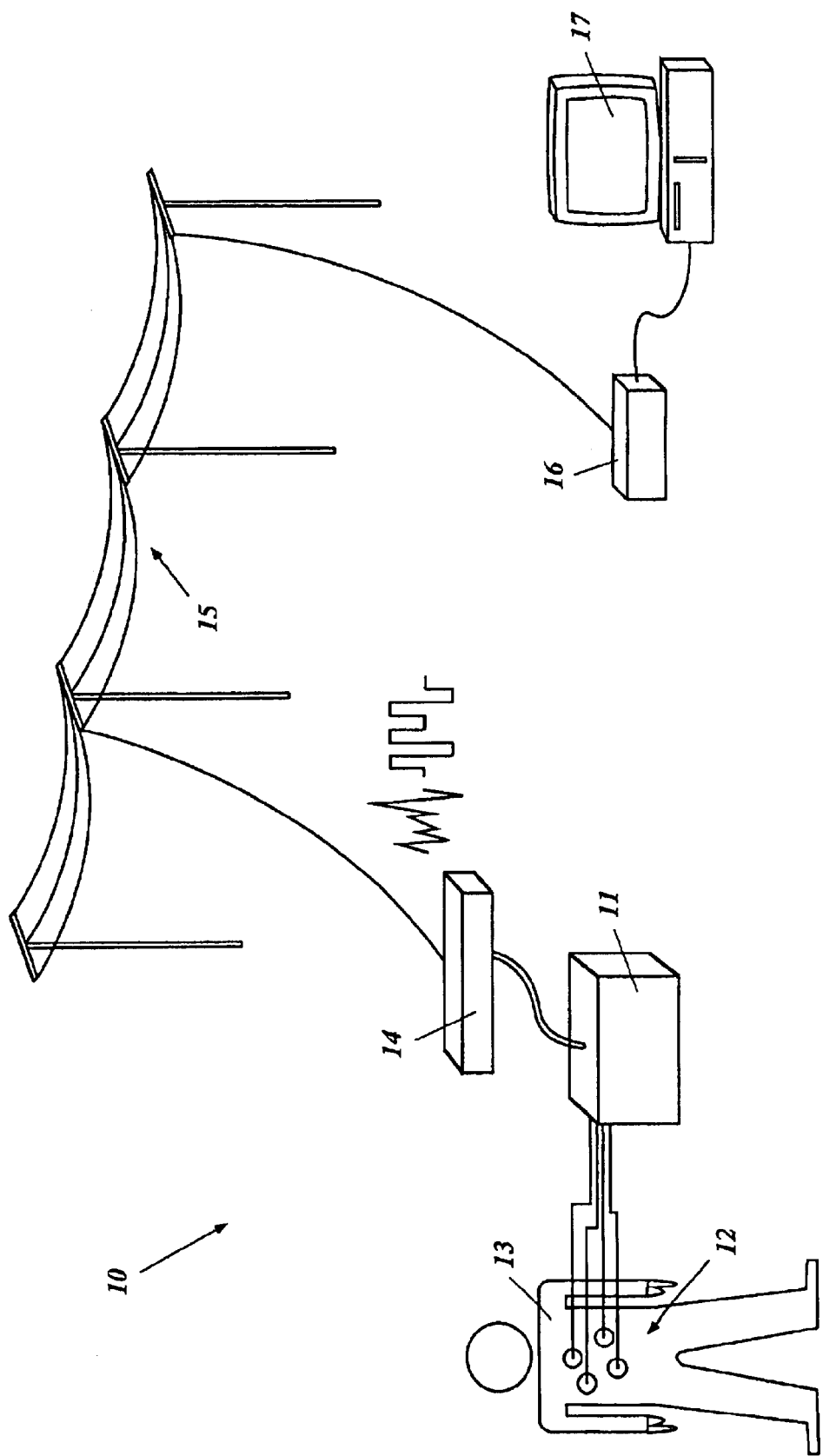
FIG. 1 is a schematic diagram of an ECG system according to a first embodiment of the invention.

With reference to FIG. 1 there is shown an ECG system 10 and ECG recording/logging device 11 adapted for connection via conducting electrodes 12 to a patient 13 whereby ECG data as one example of patient data can be acquired from the patient 13. The data is encoded, in this embodiment together with supplementary data inserted by the logging device 11, by ECG transmitter 14.

In this instance the ECG data together with the supplementary data is encoded for transmission over the Public Switched Telephone Network (PSTN) 15 whereby the ECG data is transmitted from the patient location to an analysis location at which is located ECG receiver decoder 16. The receiver decoder 16 extracts the ECG data together, in this instance, with the supplementary data from the transmission medium for supply to ECG storage and analysis device 17. In this instance the storage and analysis device 17 is in the form of a personal computer loaded with appropriate software to allow the personal computer to perform an ECG storage and analysis function.

Figure 2:
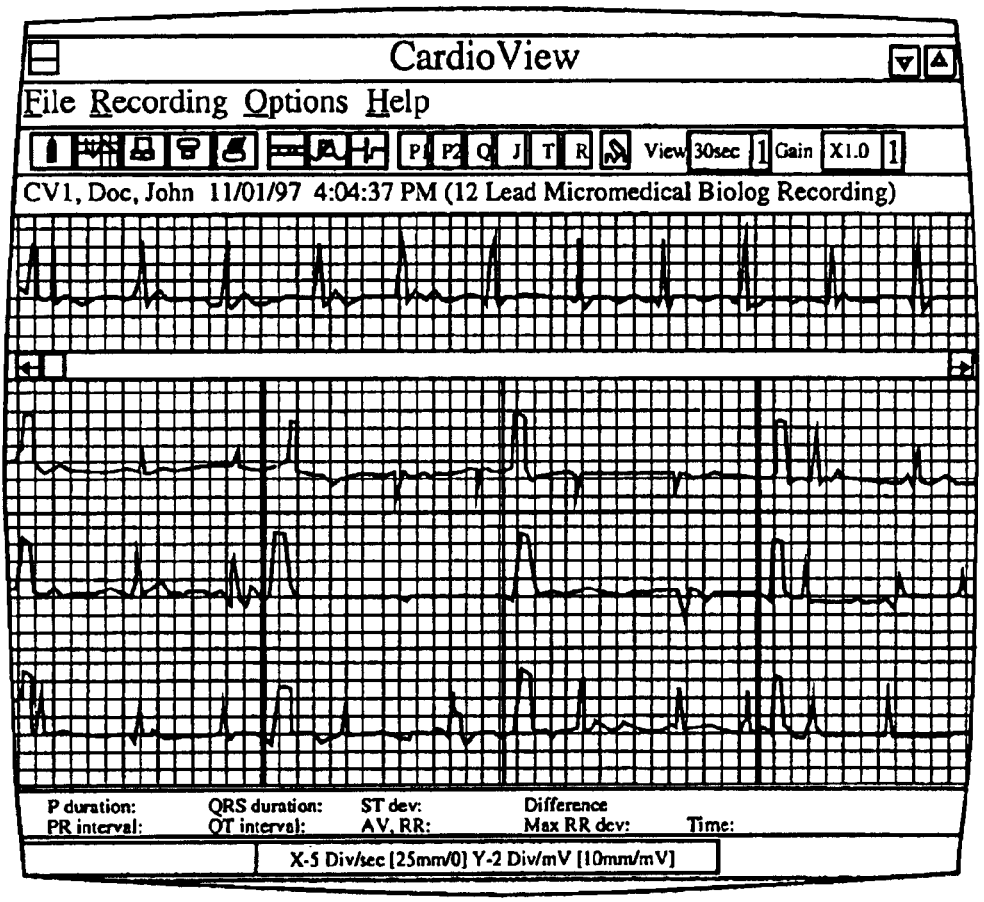
FIG. 2 illustrates typical wave forms which can be displayed and analysed by at least portions of the apparatus of FIG. 1.

FIG. 2 shows a typical display available from the ECG storage and analysis apparatus 17.

Figure 3A:
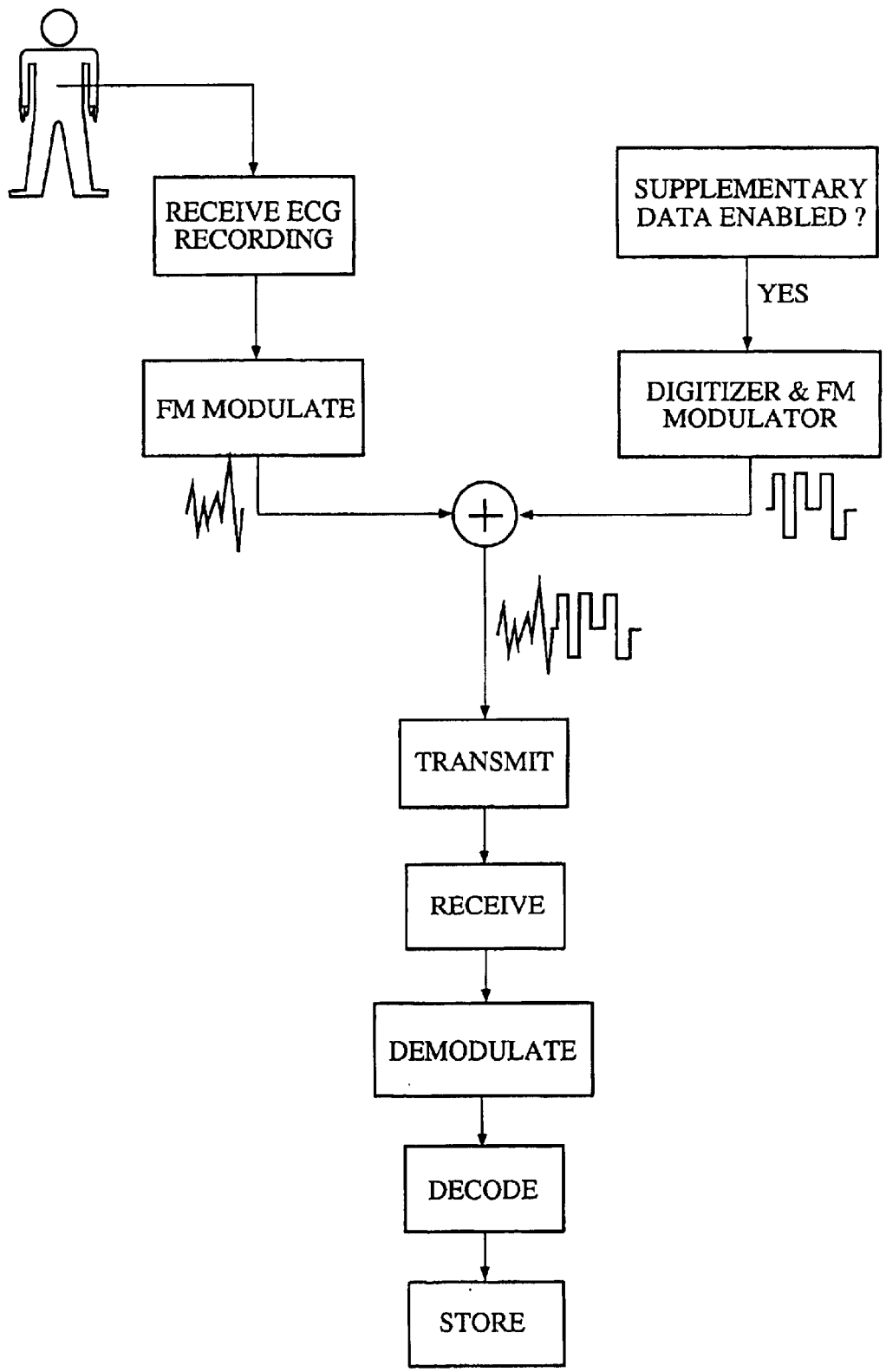
FIG. 3 is a logic flow diagram for the system of FIG. 1.
Figure 3B:
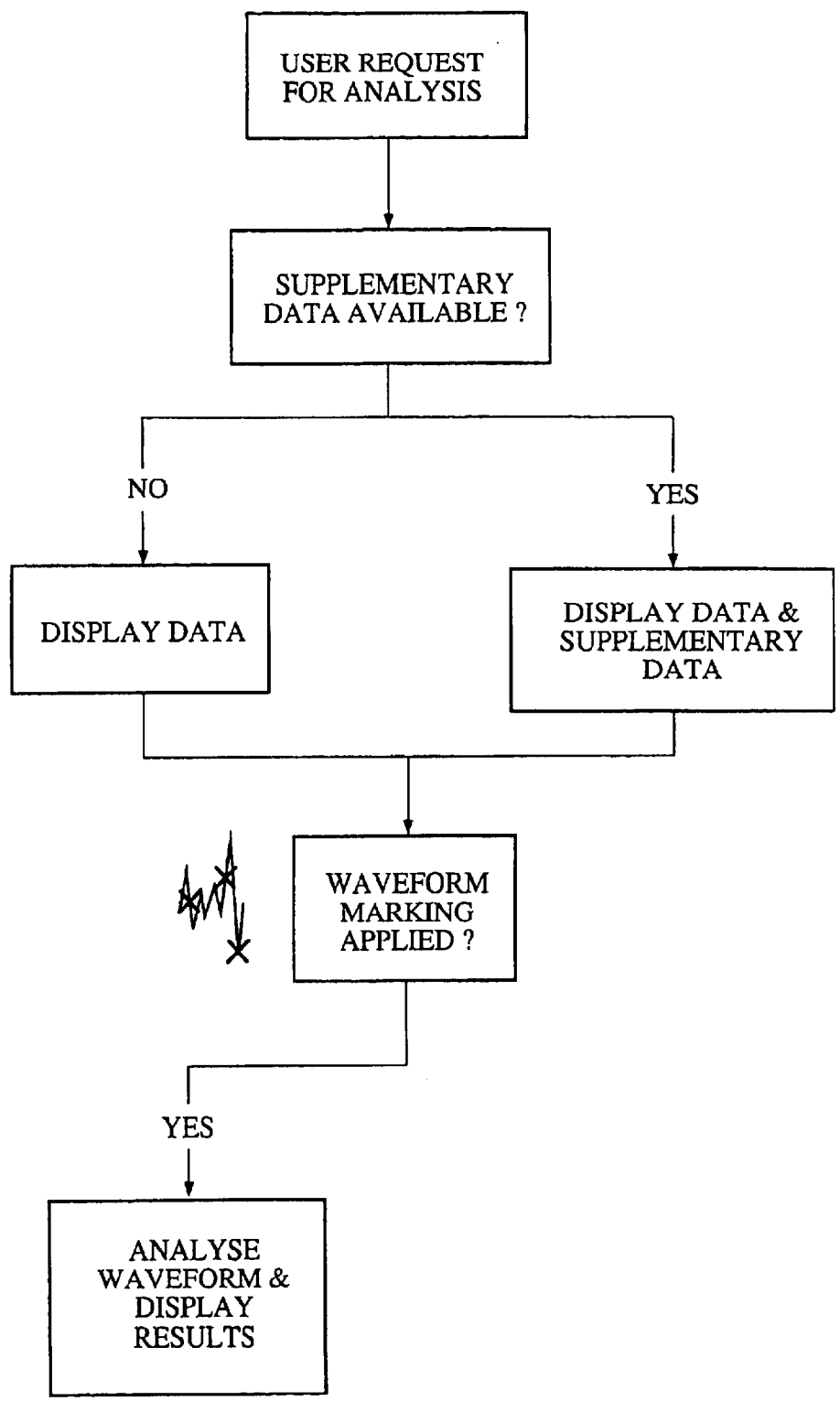

FIG. 3 is a logic flow diagram in broad form for the system of FIG. 1.

Particular aspects of this system will now be described in greater detail:

1. The Recording/Logging Device

This device can take the form of commercially available equipment adapted to manage the electrical connection to a patient and the reception of ECG signals from the patient. Suitable devices available from the assignee of the present application include the "Biolog"™ and the "Heart Tel"™ Cardiac Event Recorder.

2. The Encoder/Transmitter Device

This device performs the necessary coding and modulation to allow the ECG signal together with supplementary data to be communicated over a communications medium such as the public switched telephone network 15. In the present embodiment the ECG signal itself is encoded and modulated as an FM signal whilst supplementary data in the form of patient and station identification, date and time of ECG recording is encoded and modulated in FSK format.

3. The Receiver/Decoder Device

This device demodulates the data from its carrier in order that the data may be passed to the storage and analysis device.

4. The Storage and Analysis Device Hardware

In this embodiment the storage and analysis device takes the form of a personal computer adapted to receive the ECG and supplementary data from the receiver/decoder device by way of one or more of serial link, infared link or other bus connected communications card where forms and other data can be displayed on the PC or printed by means of printing devices connected to the PC.

Figure 4:
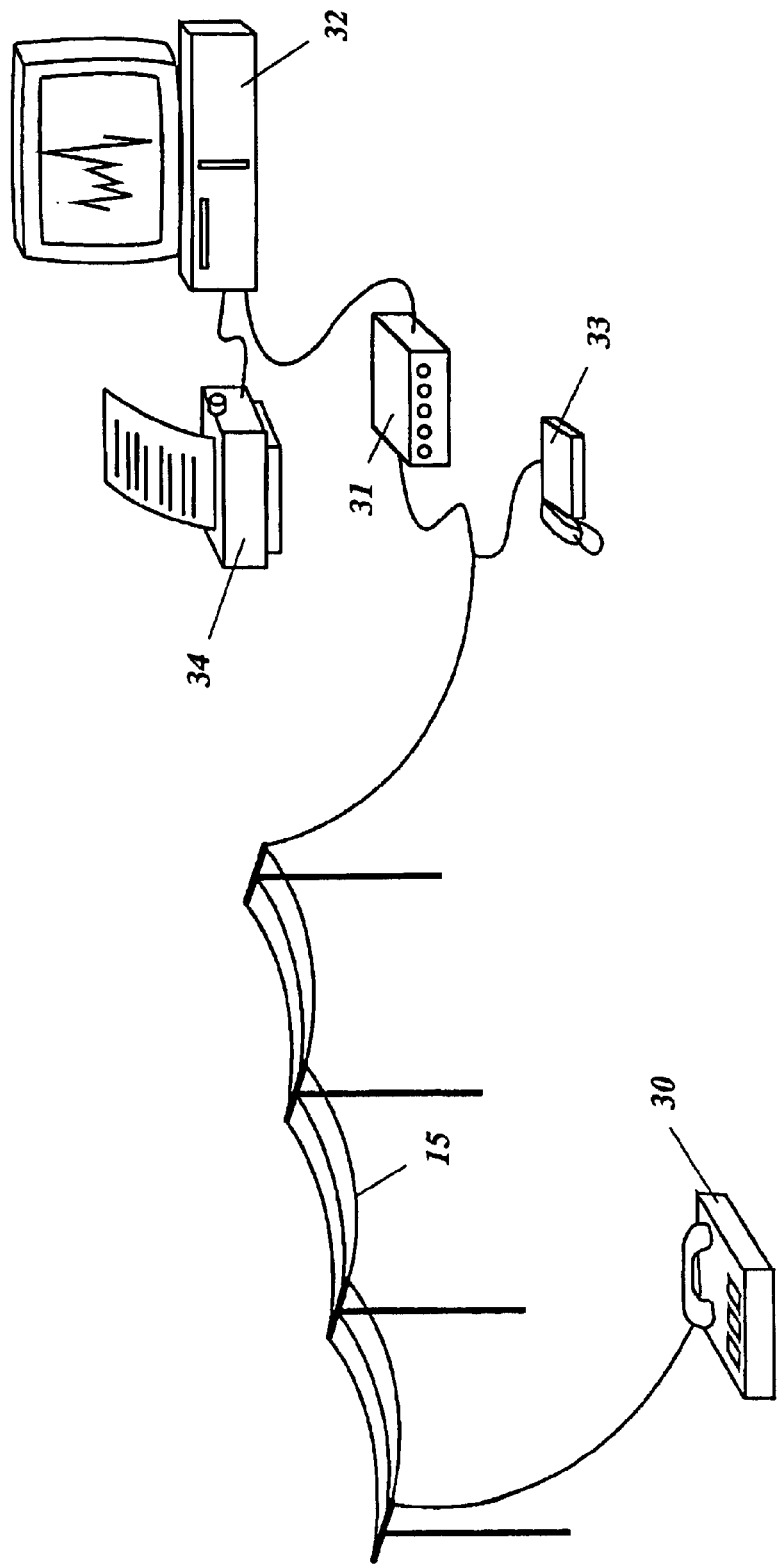
FIG. 4 is a general layout of a system according to a second embodiment of the invention.
Figure 5:
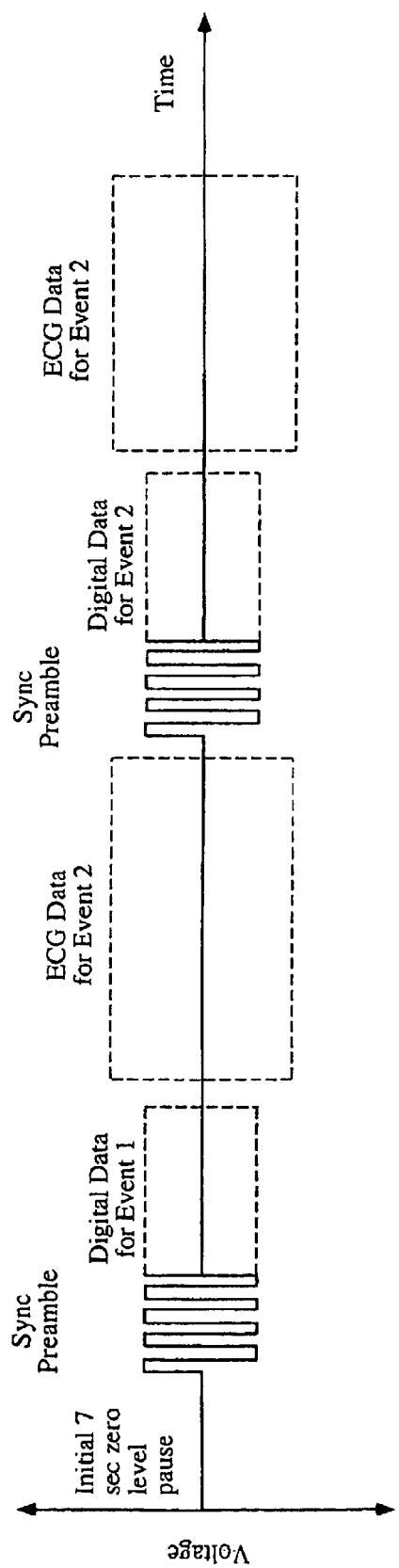
FIG. 5 illustrates a signal format suitable for use with the system of FIG. 4.
Figure 6:
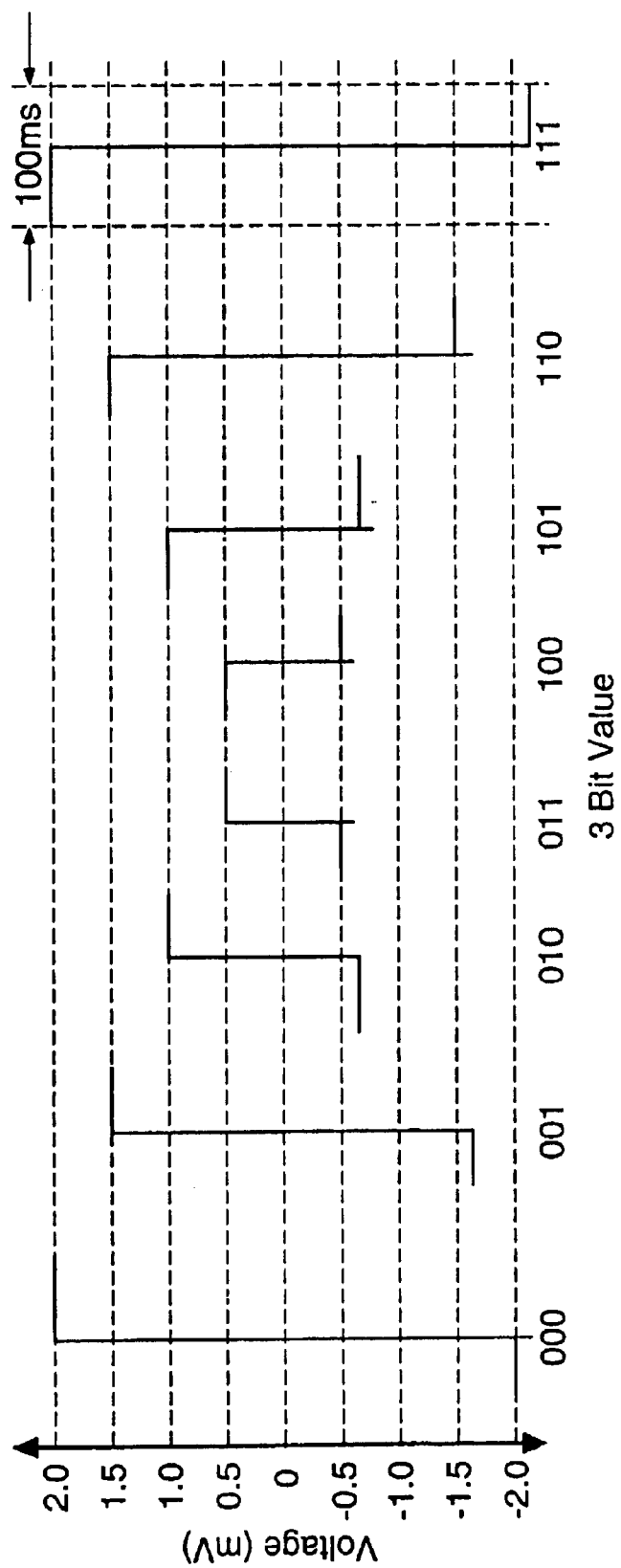
FIG. 6 illustrates signals suitable for use with the signal format for FIG. 5.

With reference to FIG. 4 a further preferred arrangement according to a second embodiment of the invention is illustrated and comprises an ECG acquisition device 30 adapted to transmit the signal format of FIG. 5 over the public switched telephone network to a demodulator unit 31 for transmission of the demodulated signal to personal computer 32. Optionally an answering machine 33 and a printer 34 can operate in parallel with the demodulator unit 31. The medical data including the ECG signal acquired by device 30 can be stored and displayed on personal computer 32 utilizing the data base software previously described.

Figure 7:
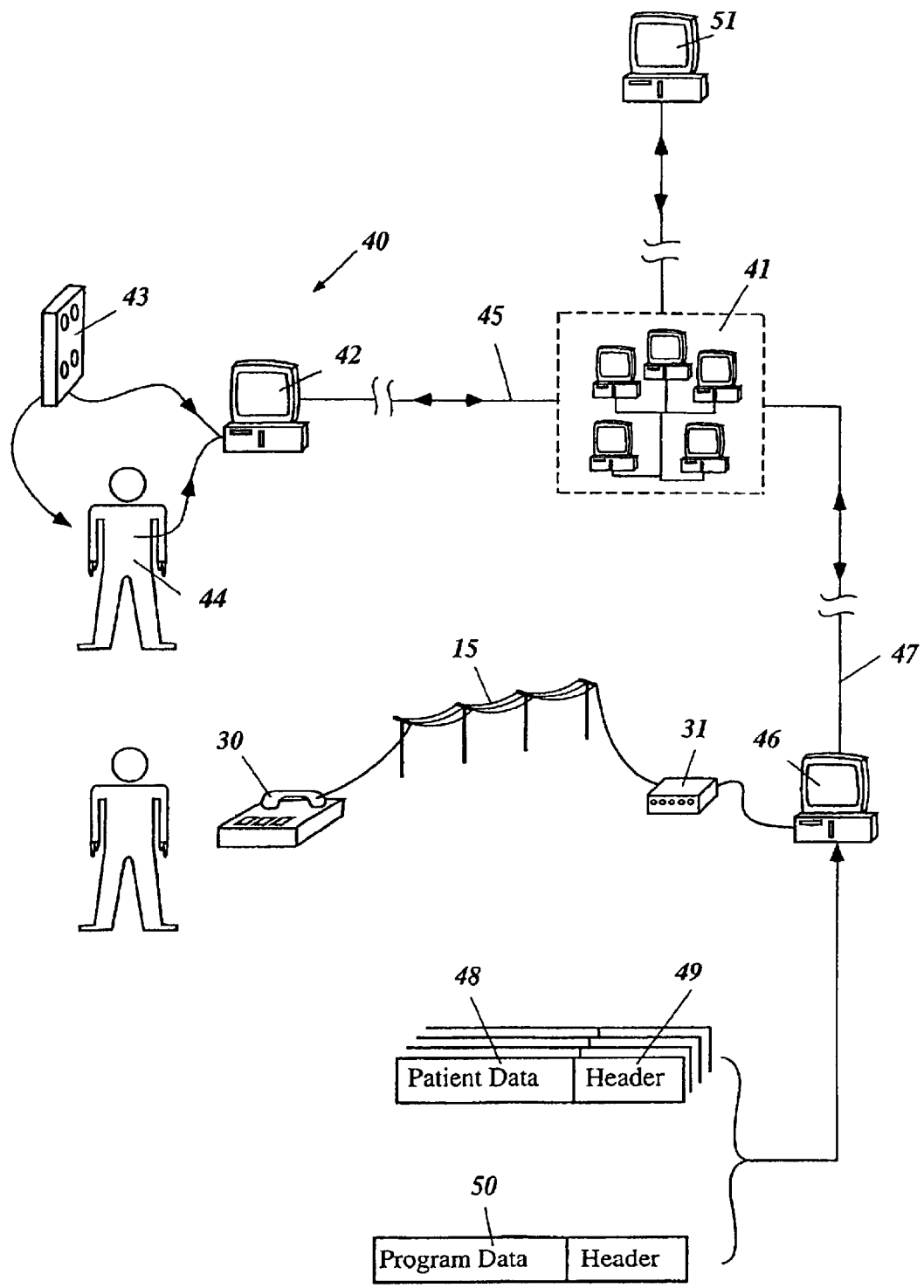
FIG. 7 is a general layout of a system according to a third embodiment of the invention implementable via the Internet.

With reference to FIG. 7 there is shown a further embodiment of the invention implementable on an interconnectable network of computers, for example of the type currently called "the internet".

The Internet in its present form is perhaps best described as an interconnectable network of computers adapted for interconnection using standardised protocols and wherein the individual computers making up the network at any given time include computers adapted to store and forward packets of digital information. The digital packets of information are thereby able to be passed from computer to computer until they reach the destination computer whose address is included as part of the packet.

In this context and with reference to FIG. 7 a telemedicine system 40 according to a third preferred embodiment of the invention is adapted for transmission and reception of patient data and supplementary data over an interconnectable network of computers of the type generally described as the internet 41.

In this instance the elements of the system 40 further include a client personal computer 42 in communication with a patient data acquisition device such as, for example, an ECG acquisition device of the type described in the applicant's U.S. Pat. No. 5,123,419. In an alternative form a patient 44 can be directly connected to the client personal computer 42 by means of a universal ECG interface cable of the type described in the applicant's co pending Australian provisional patent application entitled "Universal ECG Interface Cable" filed 10 Jan. 1997.

The client PC 42 to internet 41 connection 45 can be via the public switched telephone network as typically provided by Internet Service Providers and can take the form of an analog telephone connection, a cellular telephone connection or a cable or other broad band connection.

The system 40 further includes a central server computer 46 in communication with the internet 41 via connection 47.

The server computer 46 is adapted, as a minimum, to receive and store patient data including ECG data in the manner described in respect of the embodiments of FIG. 1 and FIG. 4 so that in its reduced form PSTN communicated information directly from ECG acquisition device 30 of the second embodiment communicating via an acoustic coupling to demodulation unit 31 and thence to central server computer 46.

The management software described with reference to the first and second embodiments can operate on central server computer 46 and in the internet implementation of the third embodiment is supplemented and enhanced with the following capabilities:

i. The ability to send and receive patient data 48 in digital packet form including destination header information 49.

ii. The ability to send program data 50 also in digitised packet form.

iii. The ability to encript or other secure at least the program data 50 to ensure its integrity on reception at destinations which can include client personal computer 42 and specialist client personal computer 51.

In a particular preferred form the program data 50 can take the form of applets such as Java (trademark) applets. In use patient data 48 comprising, for example, ECG wave forms stored at central server PC 46 and derived from client personal computer 42 can be communicated over internet 41 to specialist client PC 51. In addition programs to interpret, display and store the patient data 48 can also be sent over the internet 41 in the form of program data 50 to the specialist client PC 51 thereby ensuring appropriate and up-to-date software is utilised to perform the critical task of displaying patient data such as ECG data.

This system 40 can be implemented utilising the ActiveX set of technologies available from Microsoft Corporation. Further detail of this implementation and examples of its use is as follows.

OVERVIEW

The Server 46 uses Internet technologies from Microsoft primarily the ActiveX suite of programs and controls.

2. Architectural Overview

The most noteworthy elements in the Internet Server 46 are:

2.1 The Microsoft SQL Server Patient Data Table.

This table stores all information relevant to the patient, excluding the actual ECG recordings. The patient images are stored in the database as a series of BLOBs (Binary Large Objects) is extracted on-the-fly by an ISAPI application.

2.2 The Microsoft SQL Server ECG Data Table.

This table stores the individual ECG recordings for each patient. This includes Start/Finish times, descriptive information, etc. The ECG Data itself is stored in the database as a series of BLOBs is extracted on-the-fly by an ISAPI application.

2.3 The ECG Data Playback Application (GetPatientECG.dll).

GetPatientECG.dll is responsible retrieving the ECG data from the server for playback. For prerecorded sessions, GetPatientECG.dll writes all available ECG data to the client ActiveX control as quickly as the network infrastructure will allow.

ECG data is sent via a standard HTTP 1.0 connection, as a result of the ActiveX control issuing a GET query. If an ECG record is marked as "real-time", all data currently in the record is written to the client as quickly as the network infrastructure will allow. Once the data which was buffered in the SQL Server is sent, new data is read from the BLOB in 2K chunks as they are written to the database by the control which is recording the ECG. This process continues until he "real-time" flag is set to false, at which time, all remaining data in the SQL Server record is sent to the client. This allows users to upload data in 2K chunks, while another users (limited only by machine speed and bandwidth) are downloading. The only limitation that the 2K chunks of ECG data are inserted within a reasonable time frame such that the ECG control reading the data out of the BLOB field does not experience too high a number of "time outs". The effect is the ECG data from one client can be viewed by several other clients, with the SQL Server acting as a sort of hub. The Microsoft SQL Server 6.5 readtext, writetext, and updatetext functions allow the programmer to work with small portions of a larger BLOB, locking only the database page on which the update is occurring. Typically, the ECG files start at around 20 kilobytes in size, and can range into the hundreds of kilobytes, or into the megabytes for samples which cover the activities of a patient for an entire day. Only the writing control can cause a page to lock, and that page lock can only exist on the last page in the record; in other words, locking contention is no real issue provided all reading clients are at least 2049 bytes (or whatever the SQL Server 6.5 page size has been tuned to plus one) "behind" the writing client.

2.4 The ECG Data Record Filter (PutPatientECG.dll).

The filter is responsible for inserting new Patient ECG records into the ECG recording table.

The submission of new ECG data occurs over a standard HTTP 1.0 after the ActiveX control commences the operation with a POST query. This application operates in much the same way as the GetPatientECG.dll, but in reverse.

It is implemented as an ISAPI filter, and not an ISAPI application. In order to maintain a high level of performance, Microsoft chose to implement ISAPI applications behind several performance-enhancing buffering mechanisms. This presented a problem as Microsoft Internet Information Server continually tries to buffer all of the information it receives for a POST query, and then send it to the ISAPI application in one large chunk of data. This is not satisfactory for a real-time system.

Fortunately, ISAPI filters allow raw access to any data coming into the web server. Using a filter, it is possible to process the data in chunks, delimited by a carriage return and line feed.

3. The ActiveX Control

The ActiveX control provides the following facilities:

1. ECG Data upload and download between the Control and the ECG Server.
2. Real-time visual playback of the ECG data stream.
3. Real-time expert system processing of the ECG stream to recognise the QRS complex (patient heart beat).
4. Recording and updating of the patient's current heart rate based on the QRS detection.

The ActiveX control's architecture provides internal abstraction from the complexities of Internet and asynchronous serial communications.

As mentioned before, the control carries out all communications with the ECG server over HTTP 1.0 connections, with Microsoft Internet Information Server brokering the "transactions" between the control and the database.

To simplify the design of the demonstration system, the system does not allow end users to create new patients. Instead, an end user who wishes to record a new ECG attaches that ECG to an existing patient record. As stated, this is only a demo, so security features such as SSL and user authentication are not issues at this time.

The ActiveX control is structured in two components, ECGControl.ocx and mmidetct.dll. ECGControl.ocx is the actual control itself, and is responsible for all display and host communication functions. Mmidetct.dll provides the expert system analysis of the ECG for QRS complex (heart beat) detection. Internally, the control passes data to its own drawing routines, while simultaneously passing that data to the QRS detection dll for analysis.

3.1 The HTML and VBScript Page which instantiates and Controls the Control for Playback.

The VBScript on the playback page is responsible for bringing all of the visual user interface elements together and presenting them to the user. These elements are:
1. Setting of properties and invocation of methods on the ECGControl.
2. Analysis of heart rate with respect to patient age for aerobic exercise commentary. Presentation of this data in a floating frame.
3. Presentation of the "Patient Card" in a floating frame.
4. Presentation of the "Help" in a floating frame.
5. Presentation of the "ECG Notes" in a floating frame.

The VBScript on the record page provides an overlap in functionality with the VBScript on the playback page.

In terms of the presentation of information in the floating frame, both pages are identical. They do differentiate when it comes to how the scripts handle the ECGControl.

In the case of recording a new ECG, prior to the actual recording taking place, the VBScript sets several properties on the ECG control which effectively "let it know" what the title of the ECG is, which patient the ECG is for, and what notes should be attached. The ECG control submits this information to the database when it opens a connection to submit the first packet of ECG data.

In this example utilising active-X control the ECG records (or other patient data) are buffered in the client PC 51 prior to display. Display takes place only when sufficient data is available to provide a full ECG (or equivalent) trace for display at the same rate that the data was originally acquired. This arrangement can be described as pseudo-real-time in that the display is viewed at the same rate as recordal takes place although time delayed.

Figure 8:
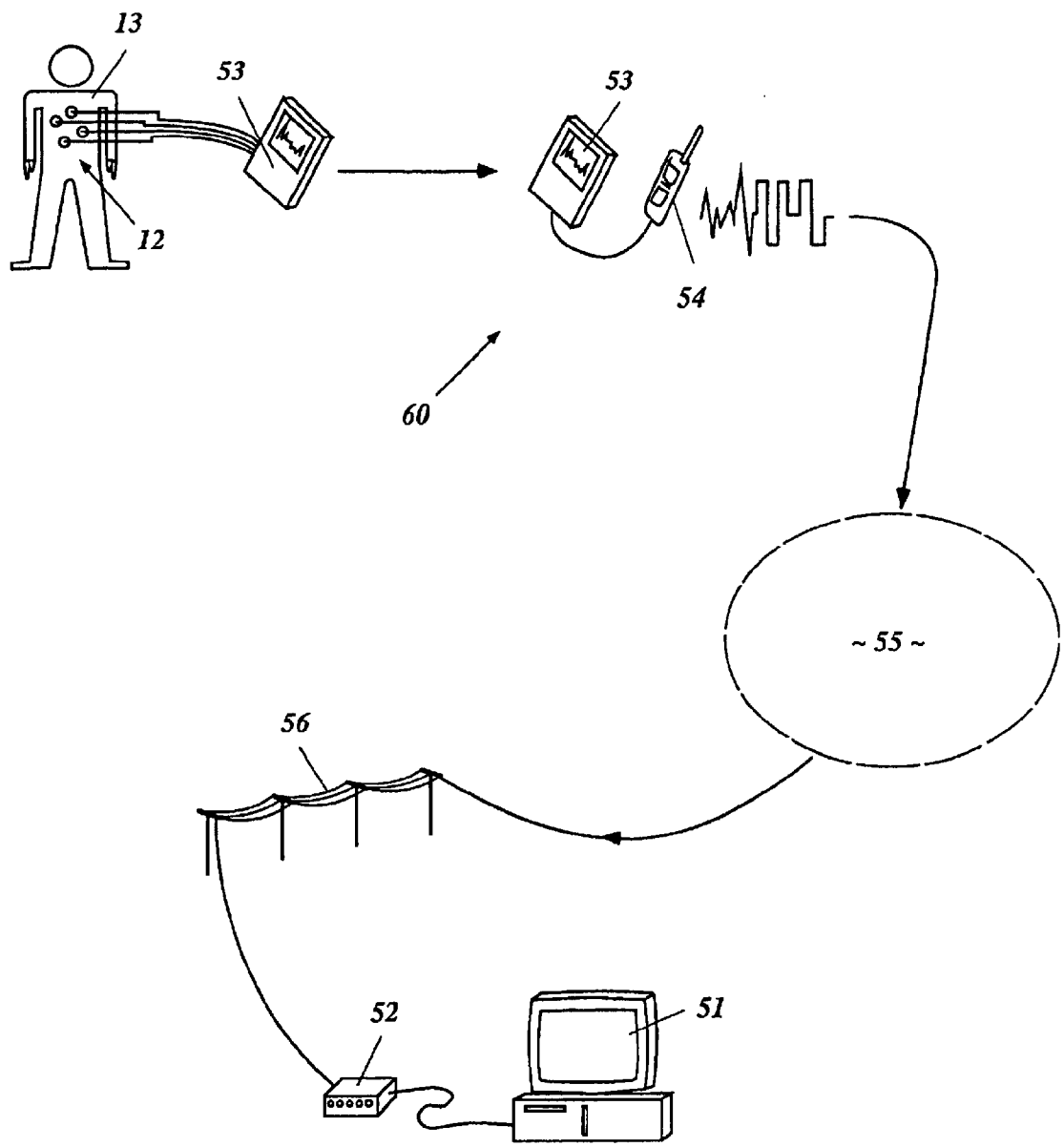
FIG. 8 is a general layout of a system according to a fourth embodiment of the invention.

With reference to FIG. 8 a telemedicine system 50 according to a fourth embodiment of the invention is illustrated in block diagram form. The system is, in essence, the same as that of the embodiment of FIG. 4 in that it uses the public switched telephone network for communication with a personal computer 51 via modem 52 operating database software.

In this instance, however, the "front end" entails use of a portable, data acquisition device such as the biolog previously described. Once patient data has been acquired by the data acquisition device 53 it is connected via its serial port to a GSM mobile phone 54. The mobile phone 54 acts as a modem for the digital data derived from data acquisition device 53 which places the digital data on the GSM mobile telephone network 55 for subsequent transmission to the public switched telephone network 56 for ultimate reception and demodulation by modem 52 and interpretation and storage on personal computer 51.

As for the Internet version previously described with reference to FIG. 7 the digital data comprising both patient data 48 and a header 49 containing supplementary data is the preferred format for transmission. A Typical format is shown in FIG. 9.

2.0 Overall Structure

The Direct Connect Serial Communications Protocol has two modes:

Command Mode:
  for establishing communications
  querying the identity and capabilities of the device
  querying and changing the configuration or operation of the device
Data Transfer Mode:
  for transferring the actual data (for example an ECG) from the device Command Mode Command mode is the default mode for the device. it is used to:
  establish communications
  query the identity and capabilities of the device
  query and change the configuration or operation of the device Communications are initialsised at 9600 baud, 8 data bit, 1 stop bit and no parity. The devices may subsequently negotiate a higher baud rate if supported.

Commands and responses in Command Mode are generally simple ASCII text, terminated by the <CR> character. Commands may be followed by a parameter(s), also simple ASCII. Command and parameters are separated by a space character. Characters are echoed by the receiving device, and a response is required to all commands. Commands are case sensitive.

The standard acknowledgment is OK. Any other response, other than a valid response or data string should be considered a "not acknowledge" or "error"

When a response (other than OK) is returned, multiple items are separated by semicolons (and terminated by a <CR>).

All devices should respond, at a minimum to ENQ, ID, DATA, and TEST.

Data Transfer Mode

Once data Transfer has been requested (by DATA command), Data Transfer Mode is started. This mode uses XModem protocol to control packet sizes, re-e\sends, and error detection. Basically, the XModem data payload contains one or more Data Blocks, similar to those specified in the Transelephone Digital Communication Protocl. These Data Blocks are appended one after another, with no padding (except possibly for the final Block). Packetisation and error checking are controlled by XModem.

Data Blocks may be broken across XModem packets, and if the final Data Block is shorter than the XModem packet size, the XModem packet is padded with (digital) zeros to the required length.

The initial character (C or G) specifies whether to use XModem or XModen-G. Packet size is determined by the initial byte in the first packet sent by the sending device (<soh>/$01=128 bytes and <stx>/$02=1024 bytes).

Data transfer is terminated by the receiving device sending two <cancel>/$18 characters, according to the XMOdem standard.

EXAMPLES

Remote Communities

Mothers in Remote Communities

A cardiotocograph (CTG) measures foetal well-being. A CTG uses two channels. One channel measures the contractions on the mothers uterus. The other channel measures the heart rate (bpm) of the foetus. These channels are both graphed side by side on a typical piece of ECG paper (long, thin strip with grid marks).

The measurement of a deceleration (slight slowing down) of the heart beat of the foetus after a contraction could indicate that the foetus has an inability to cope with stress, specifically, the high stress of birth. Other problems may be detected by beat to beat variability (regularity) of the foetus heart rate, or acceleration (slight speeding up) of the heart rate.

If no problems are detected in a foetus via a CTG, it is likely that no problems will occur in the immediate future. This gives an expecting mother some peace of mind.

While a CTG is quite different (medically) from an ECG, the data which makes up a CTG could be viewed, played back, and stored on the Internet ECG server with trivial modifications to the database and ActiveX software.

An excellent application of an Internet based CTG record/playback system would be in many of the isolated Aboriginal communities in "out back" Australia.

Many Aboriginal women feel alienated in hospitals. The environment is unfamiliar, and does not have or play a part in the traditional Aboriginal culture and life style. In some Aboriginal communities, there is a growing trend away from hospital births back to births on traditional, tribal ground.

A midwife in Arnhem land might have the ability to interpret a graph, but may not be able to distinguish many of the subtleties which may point to foetal problems.

Using this system, she could relay the information to an obstetrician in Darwin in real time, and be given on-the-spot advice.

In the instance where an aboriginal mother visits a regional health center and is made aware of potential problems, the mother can be remotely monitored over the inexpensive infrastructure of the Internet, and a flying doctor sent in if a problem is detected. The regional health center only requires access to 14400 bps data communications, which is substantially less than the requirements for existing telemedical systems.

Rare or Difficult-to-diagnose Conditions

When interpreting arrhythmia on a standard ECG, a general practitioner or nurse practitioner in a remote area may have difficulty in determining the type of arrhythmia and proper treatment. Time may be critical! A broad complex tachyarrythmia may be either a; Supraventricular tachycardia with aberrant conduction.

Ventricular Tachycardia.

Both of these conditions are extremely similar in appearance, although Ventricular Tachycardia is far more sinister and probably lethal.

Junior doctors in country areas would require specialist help in providing the correct diagnosis. A cardiologist watching in real time can interpret the ECG, provide advice, order treatment and watch the outcome remotely.

Professional and Non-professional Athletes

Professional Athletes

Professional athletes must maintain peak fitness levels to guarantee ultimate performance. Athletes training overseas in the lead-up to an international sporting event may be disadvantaged by a lack of access to resources normally available to them. They could benefit by connecting with established diagnostic facilities in their home country, via Internet Telemedicine.

Infomotion's ActiveX ECG control, Microsoft Internet Information Server and Microsoft SQL Server working in conjunction wish Micromedical's Biolog heart monitor gives athletics organisations the ability to:

Record and analyse a professional athlete's heart rate during training, performance, rest, and upon waking to make sure their training is on the right track. diagnose data from an athletes "Heart Rate Set" training, where the intended goal is to keep the heart rate at a constant level during the workout.

Determine effects of altitude and/or climatic change on the athlete's performance, and suggest alterations to the training regime if necessary.

Ensure the athlete is not overtraining.

It is conceivable that Internet Telemedicine may lead to athletes being given the opportunity to compete internationally when previously it was considered too expensive to bring over their full support team.

The above describes only some embodiments of the present invention and modifications, obvious to those skilled in the art, can be made thereto without departing from the scope and spirit of the present invention.

What is claimed is:

1. A method of communication of patient physiological data acquired from a patient, said method including the steps of arranging a predetermined communications protocol whereby patient data is communicable from a patient location to an analysis location and implemented by a system which comprises at least the following components:
   a) patient data acquisition apparatus which acquires said patient physiological data from said patient;
   b) patient data transmission apparatus which transmits said data;
   c) an interconnectable network of computers adapted for interconnection using standardized protocols and wherein the individual computers making up the network at any given time include computers adapted to store and forward packets of digital information and whereby the packets of information are thereby able to be passed from computer to computer until they reach a destination computer whose address is included as part of the packet and wherein said data is transmitted as said packets of information;
   d) a patient data server for receiving said data, said server further including a physiological database table including physiological data flagged as real-time and control means for querying said database table; and
   e) patient data storage and analysis apparatus for storing and presenting said data for analysis; said method comprising the steps of:
   i) acquiring said patient physiological data at said patient location by means of said patient data acquisition apparatus;
   ii) transmitting said patient physiological data as said packets of information by means of said patient data transmission apparatus via said interconnectable network of computers to said patient data server and storing said ECG data at said server;
   iii) processing a query for physiological data flagged as real-time; and
   iv) passing said real-time data from said patient data server to said patient data storage and analysis via the same said interconnectable network of computers.

2. The method of claim 1, wherein said patient physiological data comprises a plurality of separate wave forms acquired consecutively over a period of days or weeks.

3. The method of claim 1, wherein said storage and analysis apparatus is implemented on a personal computer.

4. The method of claim 1, wherein said patient data transmission apparatus additionally includes supplementary data insertion means for inserting supplemental data into said patient physiological data.

5. The method of claim 1, wherein a unique identifier is given to each said patient data acquisition apparatus and to said data.

6. The method of claim 1, wherein a unique identifier is given to each said patient data storage and analysis apparatus and added to said data.

7. The method of claim 6, wherein said unique identifier is embedded in a software portion comprising part of said patient data storage and analysis apparatus.

8. The method of claim 1, wherein said patient data storage and analysis apparatus includes a personal computer arranged to execute a patient data storage and analysis program.

9. The method of claim 4, wherein said patient physiological data is encoded for transmission in a first format whilst supplementary data is encoded for transmission in a second format.

10. The method of claim 8, wherein said supplementary data comprises at least one of patient data or patient data acquisition apparatus identification data.

11. A system for communication of patient physiological data from a patient location to a remote storage and analysis location, said system comprising means for transmitting said patient physiological data on a predetermined signal encoded according to a predetermined protocol whereby said patient physiological data is communicable from said patient location to said analysis location; said system further comprising:
  a) patient data acquisition apparatus for acquiring said patient physiological data from said patient;
  b) patient data transmission apparatus for transmitting said data;
  c) an interconnectable network of computers adapted for interconnection using standardized protocols and wherein the individual computers making up the network at any given time include computers adapted to store and forward packets of digital information and whereby the packets of information are thereby able to be passed from computer to computer until they reach a destination computer whose address is included as part of the packet and wherein said data is transmitted as said packets of information;
  d) a patient data server for receiving and transmitting said data, said server further including a physiological database table including physiological data flagged as real-time, and control means for querying said database table; and
  e) patient data storage and analysis apparatus for storing and presenting said data for analysis; said system containing computer readable media encoded to perform the steps of:
  i) acquiring said patient physiological data at said patient location by means of said patient data acquisition apparatus;
  ii) transmitting said patient physiological data as said packets of information by means of said patient data transmission apparatus via said interconnectable network of computers to said patient data server and storing said data at said server;
  iii) processing a query for physiological data flagged as real-time; and
  iv) passing said real-time data from said patient data server to said patient data storage and analysis apparatus via the same said interconnectable network of computers.

12. The system of claim 11, wherein said patient physiological data is transmitted as digitized packets.

13. The system of claims 12, further including a server computer adapted to receive said digitized packets of patient physiological data.

14. The system of claim 13, wherein said server computer is adapted to transmit program data and patient data in the form of digitized packets to a remote computer whereby said remote computer can execute said program data in order to display and/or interpret said patient data.

15. The system of claim 11, wherein patient physiological data is forwarded in preselected component parts and then stored for reassembly at said remote location for contiguous playback after reassembly.

16. The system of claim 11, wherein said predetermined signal includes said patient physiological data and supplementary data, said supplementary data comprising data pertaining to the circumstances of measurement of said clinical data.

17. The system of claim 16, wherein said supplementary data is digitally encoded in a wave form suitable for frequency modulation of a carrier tone in the audio range.

18. The system of claim 17, wherein said predetermined protocol includes a series of synchronization pulses which immediately precede and signal the presence of a signal containing said supplementary data.

19. The system of claim 11, wherein said predetermined signal comprises a modulated audio tone.

20. The system of claim 19, wherein said modulated audio tone is a frequency modulated (FM) audio tone.

21. The system of claim 11, wherein said predetermined protocol comprises direct modulation of an analogue wave form representing said patient data which is preceded by and recognized by a zero signal of predetermined duration.

22. The system of claim 11, wherein said patient physiological data comprises a plurality of separate ECG wave forms acquired consecutively over a period of days or weeks.

23. The system of claim 11, wherein said patient data transmission apparatus comprises a mobile telephone transmitting said patient physiological data.

24. The method of claim 1, wherein said patient data transmission apparatus comprises a mobile telephone transmitting said patient physiological data.

25. The method of claim 1, wherein said interconnectable network of computers includes the Internet.

26. The method of claim 11, wherein said interconnectable network of computers is the Internet.

* * * * *